(12) United States Patent  
Braathen et al.

(10) Patent No.: US 11,895,556 B2  
(45) Date of Patent: Feb. 6, 2024

(54) SYSTEMS AND METHODS FOR CORRELATING ENCOUNTERS BETWEEN ENTITIES VIA UBIQUITOUS NETWORKS

(71) Applicant: TEXAS INSTRUMENTS INCORPORATED, Dallas, TX (US)

(72) Inventors: Jan Morten Braathen, Redmond, WA (US); Merril Ray Newman, Schaumburg, IL (US); Timothy Wayne Simerly, Cumming, GA (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 242 days.

(21) Appl. No.: 17/410,208

(22) Filed: Aug. 24, 2021

(65) Prior Publication Data

US 2023/0063401 A1    Mar. 2, 2023

(51) Int. Cl.
```
H04W 4/02      (2018.01)
H04W 4/029     (2018.01)
G16H 50/80     (2018.01)
G06F 16/29     (2019.01)
G06F 16/28     (2019.01)
```

(52) U.S. Cl.
CPC .......... *H04W 4/023* (2013.01); *G06F 16/288* (2019.01); *G06F 16/29* (2019.01); *G16H 50/80* (2018.01); *H04W 4/029* (2018.02)

(58) Field of Classification Search
None
See application file for complete search history.

(56) References Cited

U.S. PATENT DOCUMENTS

| | | | |
|---|---|---|---|
| 11,342,051 B1 * | 5/2022 | Jain ..................... | G16H 10/60 |
| 2017/0352119 A1 * | 12/2017 | Pittman ................. | G16H 50/80 |
| 2021/0313073 A1 * | 10/2021 | McSchooler .......... | G16H 50/80 |
| 2021/0374891 A1 * | 12/2021 | Menon .................. | G08B 21/02 |

* cited by examiner

*Primary Examiner* — Adolf Dsouza  
(74) *Attorney, Agent, or Firm* — Mandy Barsilai Fernandez; Frank D. Cimino

(57) ABSTRACT

A method includes: periodically receiving data via a ubiquitous network from each of a plurality of devices, where each of the devices is associated with one of the plurality of entities and has a unique identifier; determining, as a function of the received data, a plurality of temporal locations for each of the plurality of entities, each of the temporal locations identifying a time and place where an associated entity was located; and, correlating encounters between two or more of the plurality of entities with incidence data associated with an incident, wherein an encounter is registered when a temporal location of a first of the plurality of entities is within a predefined proximity of at least a second of the plurality of entities within a physical zone associated with the incident.

27 Claims, 5 Drawing Sheets

| ACCESS POINT | LATITUDE | LONGITUDE | DEVICE ID | TIMESTAMP |
|---|---|---|---|---|
| 110-A (AP1) | $X_1$ | $Y_1$ | 120-A | 12:01:01 |
| | | | 120-B | 12:01:02 |
| | | | 120-A | 12:06:01 |
| | | | ... | ... |
| 110-B (AP2) | $X_2$ | $Y_2$ | 120-A | 12:01:01 |
| | | | 120-B | 12:01:02 |
| | | | ... | ... |
| | | | | |
| 110-C (AP3) | $X_3$ | $Y_3$ | 120-A | 12:01:01 |
| | | | 120-C | 12:06:00 |
| | | | 120-A | 12:06:01 |
| | | | ... | ... |
| | | | | |

FIG. 3-A

| DEVICE ID | TEMPORAL LOCATIONS | |
|---|---|---|
| | TIME | PLACE |
| 120-A | 12:01:01 | $f$(AP1, AP2, AP3) |
| | 12:06:01 | $f$(AP2, AP3) |
| | ... | ... |
| | | |
| 120-B | 12:01:02 | $f$(AP1, AP2) |
| | ... | ... |
| | | |
| 120-C | 12:06:00 | $f$(AP3) |
| | ... | ... |
| | | |

FIG. 3-B

SYSTEMS AND METHODS FOR CORRELATING ENCOUNTERS BETWEEN ENTITIES VIA UBIQUITOUS NETWORKS

TECHNICAL FIELD

The disclosure is directed, in general, to ubiquitous networks and devices for use with such networks and, more specifically, to novel encounter-aware applications that leverage the power of such networks.

BACKGROUND

Modern life is increasingly characterized by ubiquitous networking. Driven by new technologies such as wireless access, radio-frequency identification (RFID), cloud computing and man-machine interactions, ubiquitous networking provides the capability for person-to-person, person-to-object, and object-to-object communication anytime and anywhere. Furthermore, no longer are devices constrained to the use of specific networks with an associated subscription; open networks allow devices to automatically connect without the need for a user to provide log-in credentials.

As technology continues to advance, consumers crave the ability to monitor, track and sense more. While people's dependency on technology increases, so does frustration if they're out of wireless network range, unable to connect, or losing time with network or application installations. Companies developing connected devices often use a variety of wireless protocols, but each protocol works within a certain range and may not talk to other devices. New "mesh" networks, such as Amazon Sidewalk, can extend the range of low-bandwidth devices and make it simpler and more convenient for consumers to connect Ultimately, such mesh networks will bring more connected devices together into an ecosystem where products can all communicate on the same network. One might even prophesize that ubiquitous networks will become general infrastructure, just like power grids and pipelines, merged into people's daily lives and work, and become a key platform for economic, political, cultural, and various other socially-beneficial activities. To realize the full potential of such networks, however, it is imperative that the merits of ubiquitous interconnectivity are leveraged for the benefit of not just individuals, but society as a whole.

SUMMARY

In order to leverage the capabilities of ubiquitous networks, disclosed hereinafter is a system and method for identifying ones of a plurality of entities, such as humans, of the occurrence of an incident proximate individual ones of the entities. The method includes the steps of: periodically receiving data via a ubiquitous network from each of a plurality of devices, wherein each of the devices is associated with one of the plurality of entities and has a unique identifier; determining, as a function of the received data, a plurality of temporal locations for each of the plurality of entities, each of the temporal locations identifying a time and place where an associated entity was located; and, correlating encounters between two or more of the plurality of entities with incidence data associated with an incident, wherein an encounter is registered when a temporal location of a first of the plurality of entities is within a predefined proximity of at least a second of the plurality of entities and within a physical region associated with the incident.

The method can further include the step of adding, based on predefined criteria, registered encounters to the incidence data. Such predefined criteria can be a function of a determination that one or more temporal locations associated with an entity indicate an elevated risk of exposure to an incident; for example, an incident can be the transmission, or likely transmission, of a respiratory virus, such as SARS-CoV-2 (commonly referred to as "COVID-19"). In a related embodiment, the method can also include the step of determining, based on second predefined criteria, whether a registered encounter merits sending a notification to one or more of the plurality of entities. Alternatively, or in addition, the method can include making the incidence data accessible to each of the plurality of entities utilizing the unique identifier of their associated device.

In certain embodiments, the received data can include one or more health metrics related to an associated entity; e.g., temperature, heart rate or peripheral capillary oxygen saturation (i.e., SpO2), or significant variations in such measures. Similarly, the received data can include one or more environmental metrics related to an associated entity; such metrics can be, for example, a function the detection of carbon monoxide or other harmful gases. In certain embodiments, the data received from a device associated with an entity can also identify a second entity that has been in close proximity to the first entity; such data can also be indicative of the length of time of such proximity.

The foregoing has outlined, rather broadly, the principles of the disclosed embodiments so that those skilled in the art may better understand the detailed description of the exemplary embodiments that follow. Those skilled in the art should appreciate that they can readily use the disclosed conception and exemplary embodiments as a basis for designing or modifying other structures and methods for carrying out the same purposes of the present invention. Those skilled in the art should also realize that such equivalent constructions do not depart from the spirit and scope of the invention in its broadest form.

BRIEF DESCRIPTION OF THE DRAWINGS

For a more complete understanding of the present invention, reference is now made to the following detailed description taken in conjunction with the accompanying drawings, in which:

FIG. 3-A illustrates exemplary log data for devices from which data is received by one or more nodes of the ubiquitous network illustrated in FIG. 1;

FIG. 3-B illustrates exemplary "temporal location" data corresponding to the exemplary log data in FIG. 3-A;

DETAILED DESCRIPTION

Much like the ever-increasing presence of wireless networks in the lives of people, modern life is characterized by greater interactions between people, technologically as well as physically. In 2020, the global interconnectedness of humanity was challenged by the SARS-CoV2 virus pandemic. The initial response to the pandemic was for people to physically isolate, leading to the widespread shut-down of many businesses, causing significant hardship to those who lost their job, if not their own business. Efforts were undertaken to try to identify persons with the virus, trace their prior contacts and track any subsequent encounters; such efforts, generally manual and laborious, tended to have little effect in stemming the advance of the virus. It has been recognized that a technical solution could leverage the use of ubiquitous networks to automatically track and trace social interactions to manage future pandemics, as well as for other useful purposes. The principles of the system and methods disclosed herein provide a foundation for such purposes.

Figure 1:
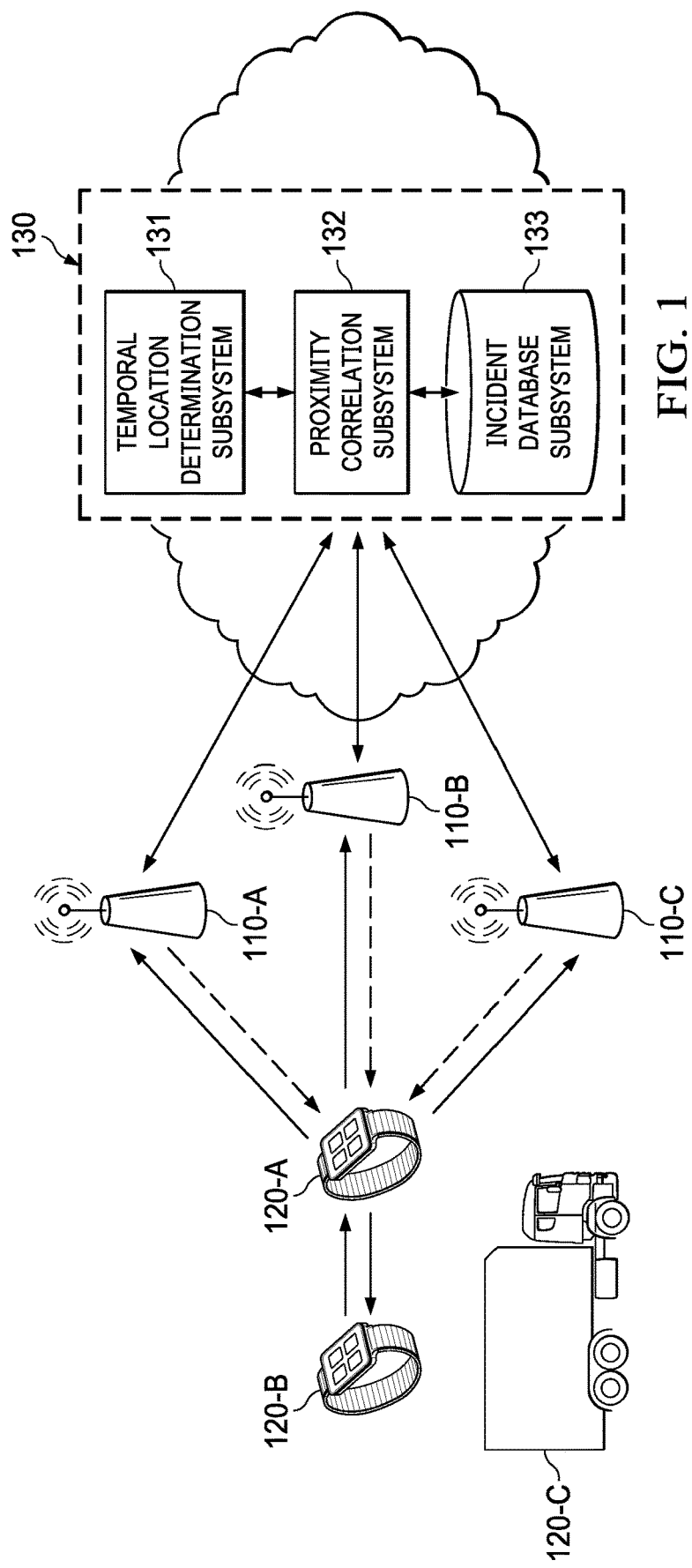
FIG. 1 illustrates a system for identifying entities of the occurrence of an incident proximate individual ones of the entities.

Referring first to FIG. 1, illustrated is a system 130 for identifying entities of the occurrence of an incident proximate individual ones of the entities. As used herein, an "entity" is anything with a distinct and independent existence; in particular, an entity can be a human. An "incident" can be any event or occurrence that could affect one or more entities; examples include, but are not limited to, viral outbreaks, hazardous material spills and radioactive leaks. An incident, however, need not be restricted to an event or occurrence that would be harmful to an entity; the incident could simply be something which a person witnessed, such as a vehicle accident or crime. Each entity has an associated device, each of which has a unique identifier (e.g., a serial number). As illustrated, a suitable device could be a wearable, such as a smart watch, two of which are shown (120-A and 120-B). In certain applications, however, an entity can be any mobile physical thing, such as a vehicle 120-C; in such cases, the device associated with the vehicle can be, for example, an electronic module attached to the vehicle, an electronic key to the vehicle, or a wireless garage door opener.

The system 130 relies on a ubiquitous network having a plurality of access points (APs), of which three are shown (110-A, 110-B, and 110-C). The access points preferably form a "mesh" network and can utilize various wireless protocols to interact with the uniquely-identified devices associated with each entity. Mesh networks can enable devices commonly connected only to a home network to effortlessly expand throughout a broader geographical area. For example, by utilizing the sub-1 GHz wireless band (900 MHz), which leverages low data rates to create a long-range, low-power network, a mesh network can make it possible for consumers to expand network connectivity outside their home and stay connected to their other networked devices. The extended range can alleviate concerns of dropping connectivity and expands the use cases for connected devices. To complement the sub-1 GHz protocol, such mesh networks and devices can also utilize Bluetooth®. Low Energy (BLE) to provide even greater connectivity, both between devices and access points and directly between devices (e.g., between device 120-A and 120-B). One commercially-available device embodying those technologies is Texas Instruments® CC 1352R. SimpleLink™ High-Performance Multi-Band Wireless MCL.

With continuing reference to FIG. 1, the system 130 for identifying entities of the occurrence of an incident proximate individual ones of the entities includes a temporal location determination subsystem 131, a proximity correlation subsystem 132, and an incident database subsystem 133. As will be described hereinafter with reference to FIGS. 2, 3-A and 3-B, temporal location determination subsystem 132 is operative to determine, as a function of data received from each device (e.g., 120-A and 120-B), a plurality of temporal locations for the associated entities, each of the temporal locations identifying a time and place where each entity is or was located. Proximity correlation subsystem 132, which will be explained with reference to FIGS. 3-B and 4, is operative to correlate encounters between two or more of the plurality of entities with incidence data associated with an incident, wherein an encounter is registered when a temporal location of a first of the plurality of entities is within a predefined proximity of at least a second of the plurality of entities and within a physical region associated with an incident. Incident database subsystem 133 maintains records of incidents of interest; it can also maintain logs of encounters between two or more entities, which can be added based on predefined criteria. Although the temporal location determination subsystem 131, proximity correlation subsystem 132, and incident database subsystem 133 are each illustrated as separate units, the functionality can be combined into one physical system or distributed across multiple physical computing devices or systems; furthermore, each subsystem can be implemented as a stand-alone computer processing system or as software functionality hosted in a cloud processing system. In all implementations, each subsystem comprises at least instructions stored in a computer memory which, when executed by a processor, are operative to perform the functions described herein; no limitations are placed on the specific means for executing such functionality. Suitable processing resources can include one or more microcontrollers, application specific integrated circuits (ASICs), central processing units (CPUs), graphics processing units (GPUs), and/or other processing resources configured to execute instructions stored in one or more non-transitory computer-readable media; examples of such media include flash memory devices, battery-backed random access memory (RAM), solid-state drives (SSDs), hard disk drives (HDDs), optical media, and/or other memory devices suitable for storing the instructions for the processing resources.

Figure 2:
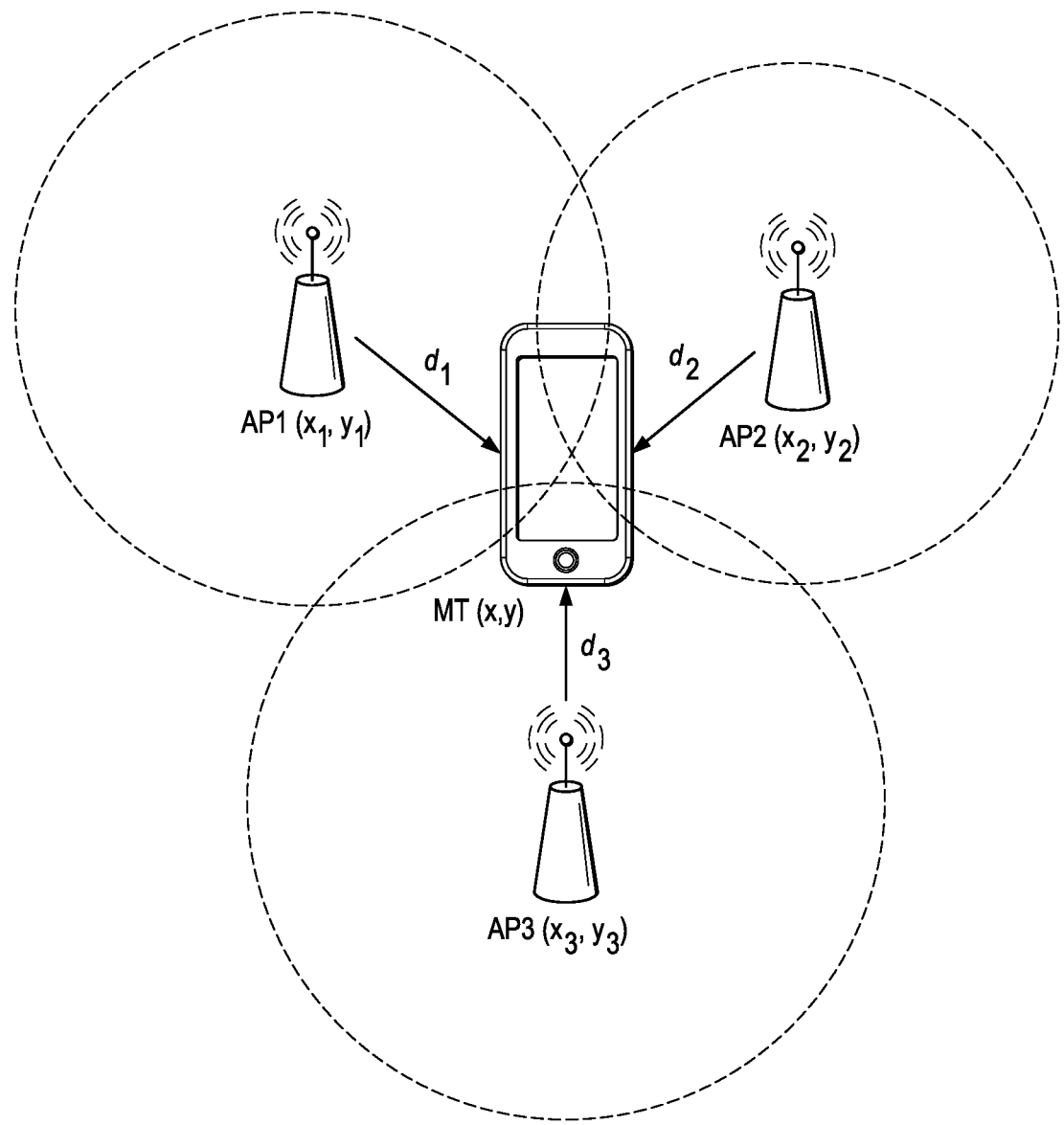
FIG. 2 illustrates the general principles of trilateration for the positioning of a wireless device.

Determining the location of a device can be realized either through onboard technology, through network-based functionality, or a combination of onboard and network functionality. Onboard technology, for example, can be through the use of a Global Positioning System (GPS) receiver. Because GPS receivers require a lot of power, however, many applications preferably utilize network-based functionality; in such systems, several receiver stations measure the signals transmitted from each wireless device and relay the information to a central site for processing to calculate a device's location. Referring to FIG. 2, illustrated are the general principles of trilateration for the positioning of a wireless device; e.g., a "mobile terminal" (MT). Depending on its physical location (x, y), a MT has access to one or more wireless access points (AP), such as access points AP1, AP2 and AP3. As illustrated, AP1 is located at $x_1$, $y_1$; AP2 is located at $x_2$, $y_2$; and, AP3 is located at $x_3$, $y_3$. The distance of the MT from access points AP1, AP2 and AP3 is $d_1$, $d_2$ and $d_3$, respectively. Utilizing knowledge of the respective physical locations of the access points, and the strength of signals received by an access point from a device, the physical location of the device can be estimated; the more access points within range of a device, the more accurate the position estimate. For example, if a device is only within range of AP1, then its location can only be determined to be within a circle centered on $x_1$, $y_1$ having radius $d_1$ (for some access points having sectorized antennas, the location might be more accurately determined to be within a given sector of the circle); the radius can be computed, for example, as a function of received signal strength. If the device has further access to a second access point, such as AP2, the location of the device can be more accurately determined to be within the region of overlap of circular regions associated with AP1 and AP2. The most precise determination of a device's location is if it is within range of at least three access points; as illustrated in FIG. 3-A, for example, the device location is the point corresponding to the intersection of the three regions associated with access points AP1, AP2 and AP3, where the distances $d_1$, $d_2$ and $d_3$ are computed as a function of the received signal strength from the device at access points AP1, AP2 and AP3, respectively. Those of ordinary skill in the art are familiar with the various techniques for wireless positioning of devices and further details are unnecessary herein to understand the principles of the present disclosure.

Referring now to FIG. 3-A, illustrated is exemplary log data for devices from which data is received by one or more nodes 110-A, 110-B, and 110-C of the ubiquitous network illustrated in FIG. 1; the nodes, for purposes of illustration, also correspond to access points AP1, AP2 and AP3 illustrated in FIG. 2. As illustrated, device 120-A was connected to AP1 at times 12:01:01 and 12:06:01; connected to AP2 at 12:01:01; and connected to AP2 at 12:01:01 and 12:06:01. Being "connected" to an access point can mean, for example, that the device 120-A emitted a beacon signal that was received by the access points at the indicated times (illustrated as unidirectional solid lines between a device and an access point or other device in FIG. 1); a full connection, however, includes a reverse link (illustrated as a unidirectional dashed line in FIG. 1). A beacon signal can be, for example, transmitted by a device at 5 minute intervals; the length of the beacon interval can be a function the power capabilities of the device, with longer intervals preferable for devices with limited battery power. Thus, as illustrated, device 120-A emitted a beacon signal at a 5 minute interval, remaining within range of access points AP1 and AP3, but moving out of range of AP2 after transmission of the first beacon signal at 12:01:01. Similarly, device 120-B emitted a beacon signal at 12:01:02, which was received by AP1 and AP2, but not by AP3; and, device 120-C emitted a beacon signal at 12:06:00, which was received by AP3, but not by either of access points AP1 or AP2. Based on the exemplary log data, it can be determined that devices 120-A and 120-B were physically proximate to each other during a time period around 12:01; similarly, it can be determined that devices 120-A and 120-C were physically proximate to each other during a time period around 12:06. From the exemplary log data, there is no indication that device 120-B was ever physically proximate to device 120-C; device 120-A, however, was physically proximate to device 120-C after being physically proximate to device 120-B. Thus, it can be recognized that encounters between multiple devices can be tracked over time; i.e., personal contacts can be traced, such as between device 120-C and 120-A, which had contact with device 120-B five minutes previously.

The exemplary log data illustrated in FIG. 3-A can be utilized to compute a series of temporal locations for each device; as used herein, a temporal location identifies a time and place where an entity associated with a device was located. FIG. 3-B illustrates temporal location data corresponding to the exemplary log data in FIG. 3-A. For example, as noted supra, device 120-A emitted a beacon signal that was received by each of access points AP1, AP2 and AP3 at 12:01;01. Accordingly, the location of device 120-A at that time is a function of signals received by those three access points; i.e., $f$ (AP1, AP2, AP3). That location would be the point defined by the distances $d_1$, $d_2$ and $d_3$ from access points AP1, AP2 and AP3, respectively, computed as a function of the received signal strength from the device at the access points. Similarly, the temporal location of device 120-A at time 12:06:01 would be a function of signals received by access points AP2 and AP3; i.e., $f$ (AP2, AP3). Finally, the temporal location of device 120-B at time 12:01:02 would be a function of signals received by access points AP1 and AP2—i.e., $f$(AP1, AP2); and, the temporal location of device 120-C at time 12:06:00 would be a function of signals received by access point AP3—i.e., $f$ (AP3).

Figure 4:
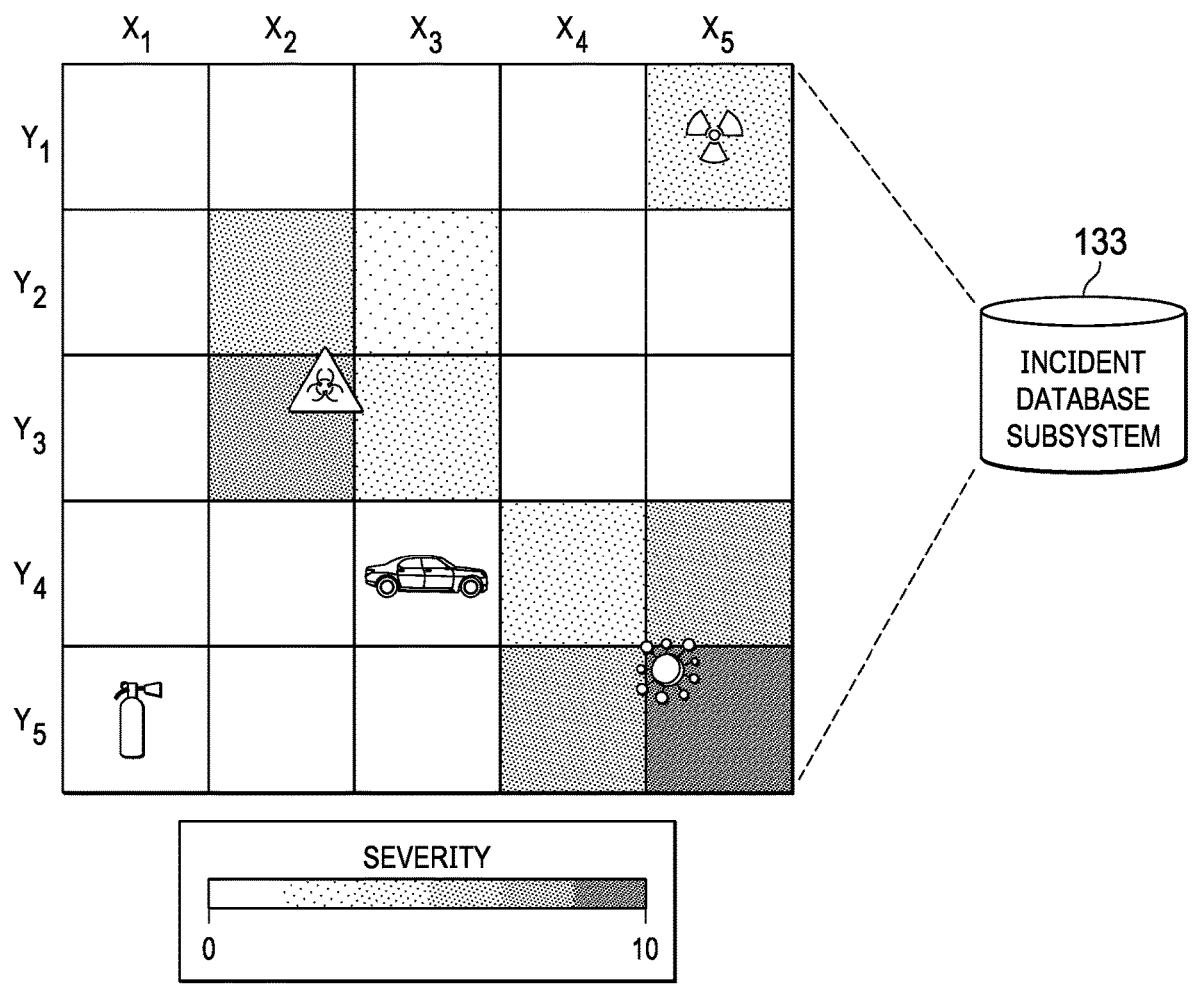
FIG. 4 illustrates exemplary contents of an Incident Database Subsystem; and, FIG. 5 illustrates an exemplary method for identifying entities of the occurrence of an incident proximate individual ones of the entities.

Turning now to FIG. 4, illustrated is incident database subsystem 133, which is operative to store incidence data associated with one or more incidents. As used herein, an incident can be any event or occurrence that can be encountered by an entity; in particular, the occurrence, rate or frequency of a disease, accident, crime, or something else undesirable. The data associated with an incident and stored in the incident database subsystem 133 generally includes one or more geographical locations associated with each incident; the data can further include a severity rating (illustrated in FIG. 4 by a grayscale ranging from 0 to 10) for the incident at each location as well as temporal data identifying the time, or period of time, associated with an incident. For example, as illustrated in FIG. 4, a biological-related incident (e.g., a hazardous material leak) can be identified as affecting a geographical region defined by areas $x_2$, $y_2$; $x_2$, $y_3$; $x_3$, $y_2$; and, $x_3$, $y_3$—the area with the highest severity being $x_2$, $y_3$. Temporal data (not shown) associated with the biological-related incident can be correlated with measurements in each area to determine movement of the biological hazard; for example, as illustrated, it appears that the biological incident originated in area $x_2$, $y_3$ and migrated into adjacent areas, possibly carried by wind currents. Similarly, an automobile incident is indicated as occurring in area $x_3$, $y_4$; and, a fire incident is indicated as occurring in area $x_1$, $y_5$. Finally, a viral incident (e.g., SARS-CoV-2 infection) is indicated as occurring in the geographical region defined by areas $x_4$, $y_4$; $x_4$, $y_5$; $x_5$, $y_4$; and, $x_5$, $y_5$—the area with the highest severity (e.g., greatest number of confirmed infections) being $x_5$, $y_5$. These exemplary types of incidents will be further described hereinafter with respect to various use cases for the principles disclosed herein.

Figure 5:
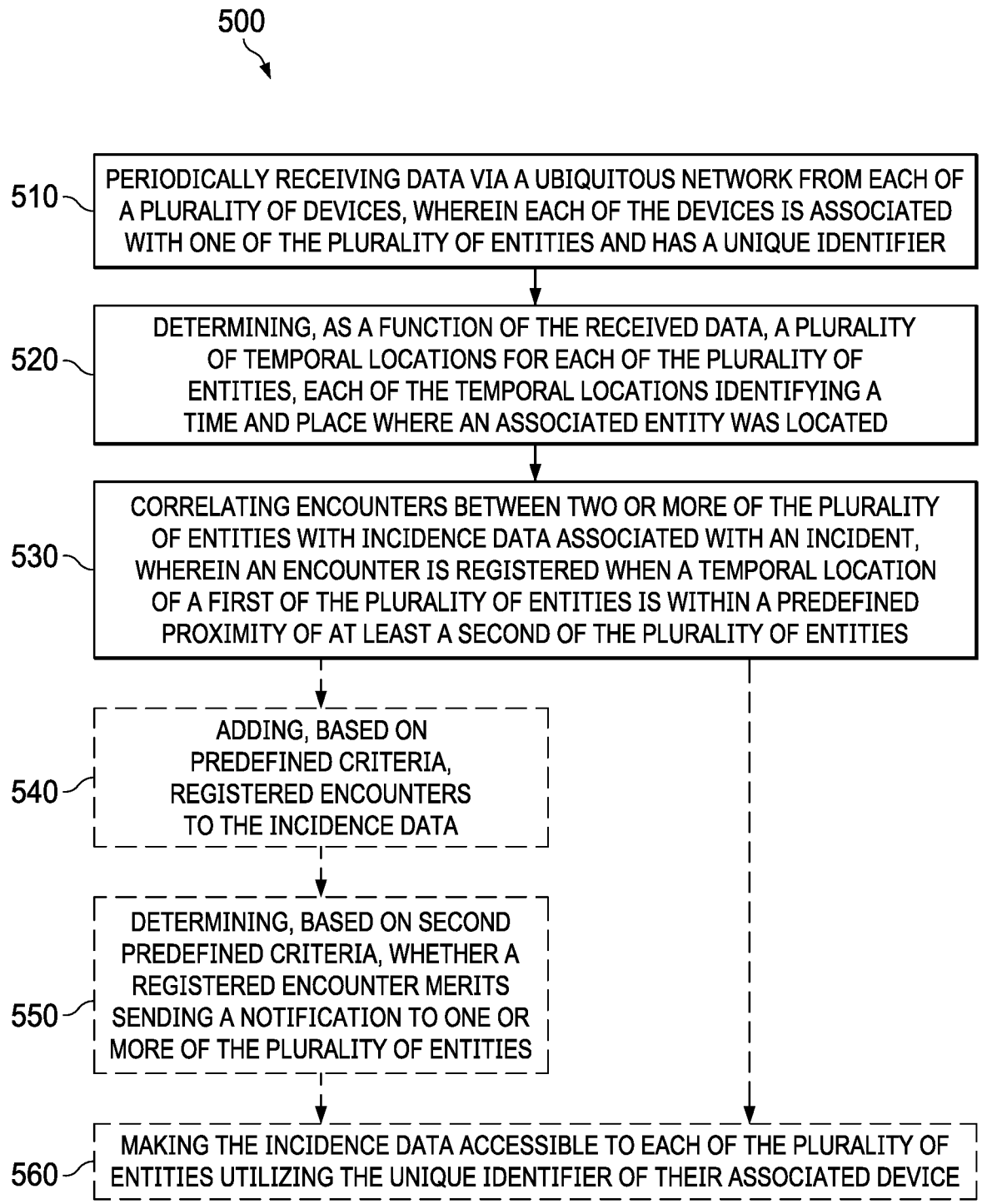

Referring now to FIG. 5, illustrated is an exemplary method 500 for identifying entities of the occurrence of an incident proximate individual ones of the entities. The method includes functions that can be embodied in digital code stored in one or more memories accessible by one or more processors for execution thereof, such as within temporal location determination subsystem 131, proximity correlation subsystem 132, and incident database subsystem 133 illustrated in FIG. 1 and described supra. The method 500 begins in step 510, wherein data is periodically received via a ubiquitous network (e.g., access points 110-A, 110-B, and 110-C) from each of a plurality of devices (e.g., 120-A and 120-B), wherein each of the devices is associated with one of the plurality of entities and has a unique identifier; the data is received by system 130. In addition to a unique identifier for each device, the data that is periodically received can further include, for example, global positioning system (GPS) location data and/or health or environmental metrics as described hereinafter. Next, in step 520, temporal locations are determined, as a function of the received data, for each of the plurality of entities, wherein each of the temporal locations identifies a time and place where an associated entity was located; see, for example, FIGS. 3-A and 3-B and the description related thereto supra. In the exemplary system 130, step 520 is performed by temporal location determination subsystem 131. In step 530, encounters between two or more of the plurality of entities are correlated with incidence data associated with an incident, wherein an encounter is registered when a temporal location of a first of the plurality of entities is within a predefined proximity of at least a second of the plurality of entities and within a physical region associated with the incident. As an example, the geographical locations of various incidents, as illustrated in FIG. 4, stored in incident database subsystem 133 can be overlayed on temporal locations of devices, as illustrated in FIG. 3-B, that are determined by temporal location determination subsystem 131.

The method 500 can further include step 540, wherein registered encounters between devices can be added to the incidence data based on predefined criteria. For example, such predefined criteria can be a function of a determination that one or more temporal locations associated with an entity indicate an elevated risk of exposure to an incident—for example, an incident can be the transmission, or likely transmission, of a respiratory virus, such as SARS-CoV-2. In a related embodiment, the method 500 can also include step 550, wherein a determination is made, based on second predefined criteria, whether a registered encounter merits sending a notification to one or more of the plurality of entities. For example, based on a positive test for Covid-19 by an entity, secondary predefined criteria could be a registered encounter with another entity within a given time period (e.g., two weeks) prior to the positive test; a notification could be sent to all affected entities within that time period, possibly encouraging those entities to self-isolate, get tested, or take other precautionary measures. The notification could be sent either directly to a device associated with an entity or to a registered secondary means (e.g., e-mail or mobile telephone). Alternatively, or in addition, the method 500 can include making the incidence data accessible to each of the plurality of entities utilizing the unique identifier of their associated device; this functionality would allow entities that wish to remain anonymous to check the incident database for identification of any incidents possibly affecting them of which they might want to be aware.

In certain embodiments, the data received in step 510 can include one or more health metrics related to an associated entity; e.g., temperature, heart rate or peripheral capillary oxygen saturation (i.e., SpO2), or significant variations in such measures; those measurements are currently available using devices such as a Garmin® fenix® 6 multi-sport fitness watch. Such health metrics, in particular low SpO2, can be indicative of Covid-19; thus, such measurements, correlated with one or more encounters with others identified as infected by SARS-CoV-2, could be helpful in identifying an infection and tracing potential other infections. Similarly, the data received in step 510 can include one or more environmental metrics related to an associated entity; such metrics can be, for example, a function of the detection of carbon monoxide or other harmful gases by a device. Finally, the data received in step 510 can also identify a second entity that has been in close proximity to the first entity; and, such data can be indicative of the length of time of such proximity. This capability can be realized, for example, through utilization of Bluetoothk® Low Energy (BLE), whereby a device can detect the nearby presence of a second device, the identify of which it can then relay to system 130. For example, devices 120-A and 120-B may not always be within range of an access point (e.g., 110-A, 110-B, or 110-C); one or both of those devices, however, could log encounters with the other device and transfer data indicating such encounter the next time it is within range of an access point, thus ensuring a more accurate record of encounters between entities.

The foregoing has described essential and optional principles suitable for novel encounter-aware applications that can leverage the power of ubiquitous networks. There are many further potential use cases, of which the following are illustrative.

Vehicle Collisions: It is often the case that many people witness a collision between vehicles; due to the movement of traffic, however, those persons may soon move past the incident and not be known to investigators. Using the principles disclosed herein, vehicles could be provided with a device suitable to provide data to a ubiquitous network to log its temporal location; the device could be integral to the vehicle, or it could be associated with an occupant—either the driver or a passenger. Alternatively, the device could be attached to the vehicle, such as an automatic toll tag or a data logging device some insurers now offer as an option or mandate for certain drivers. After a vehicle incident, the incident location and time could be entered into an incident database and correlated to temporal location data of other vehicles and/or persons who were within a defined proximity of the vehicles involved in the collision at the time of the incident. The persons associated with the devices or vehicles whose temporal location data indicates they may have witnessed the collision could then be contacted to potentially aid in investigation of the collision.

Crimes: The foregoing example could also be adapted to the investigation of crimes. In some cases, persons proximate to the perpetration of a crime may not be aware that a crime took place; however, they may have observed something that could be useful to investigating the crime. For example, a person may observe a vehicle travelling at an excessive speed, of which they might make a mental note. Later, if contacted by investigators of a bank robbery in the vicinity shortly before the person observed the speeding vehicle, the person might recall the make and model of the vehicle, thus, aiding in the investigation. Thus, using the principles disclosed herein, a device associated with such persons, such as a smart watch or mobile telephone, could automatically provide data to a ubiquitous network to log its temporal location, which information could later be used by investigators to identify potential witnesses to aid in solving a crime.

Terrorism: An unfortunate reality of our modern world is the ever-present specter of a terrorist incident; of particular concern is the potential use by terrorists of a biological agent or radioactive "dirty bomb". An array of devices, both stationary and mobile, could be deployed with environmental sensors and, utilizing the principles described herein, be useful in identifying and tracking the movement of persons or vehicles carrying a biological or radiological contaminate.

Gaming/Simulation: The principles disclosed herein can also be utilized for entertainment or simulation purposes. For example, an "incident" can be simulated, and is not necessarily of a negative nature; alternatively, an incident can be related to an actual event, and encounters between individuals can be registered and correlated to the simulated or actual event for gaming purposes. Simulations could, for example, be used to test theories of virus propagation. A gaming scenario could award points for accumulating encounters based on some criteria defined by the game rules.

The technical principles disclosed herein provide a foundation for novel encounter-aware applications that leverage the power of ubiquitous networks. The exemplary embodiments presented herein illustrate the application of the technical principles and are not intended to be exhaustive or to be limited to the specifically-disclosed applications; it is only intended that the scope of the technical principles be defined by the claims appended hereto, and their equivalents.

We claim:

1. A method comprising:
   receiving, by a plurality of access points (APs) of a network, beacons from a plurality of devices, wherein each of the plurality of devices has a unique identifier;
   storing a plurality of temporal locations associating each of the plurality of devices with associated beacon reception times and beacon reception APs;
   correlating the plurality of temporal locations with an incident database to determine temporal and physical overlap between incidents of the incident database and the plurality of temporal locations; and
   reporting data based on the correlating.

2. The method of claim 1, further comprising adding a first encounter to the incident database when a temporal location of a first device of the plurality of devices is within a predefined proximity of a second device of the plurality of devices and within a physical region associated with an incident of the incident database.

3. The method of claim 1, wherein reporting data based on the correlating comprises providing a first notification to a first device of the plurality of devices having temporal and physical overlap with an incident of the incident database.

4. The method of claim 3, wherein the first notification comprises information about measures for an entity associated with the first device to take.

5. The method of claim 1, further comprising making incidence data of the incident database accessible to each of the plurality of devices.

6. The method of claim 1, further comprising adding a first encounter to the incident database based on a determination that one or more temporal locations associated with a device of the plurality of devices indicate an elevated risk of exposure to a first incident of the incident database.

7. The method of claim 6, wherein the first incident comprises transmission of a respiratory virus.

8. The method of claim 1, further comprising receiving, from a first device of the plurality of devices, first data identifying an entity that has been in close proximity to the first device.

9. The method of claim 8, wherein the first data is further indicative of the length of time of such proximity.

10. The method of claim 1, wherein the network is a ubiquitous network.

11. The method of claim 1, further comprising associating each of the plurality of devices with a respective entity of a plurality of entities.

12. The method of claim 11, further comprising periodically receiving, from a first device of the plurality of devices, one or more health metrics related to an associated entity of the plurality of entities.

13. The method of claim 11, further comprising periodically receiving, from a first device of the plurality of devices, one or more environmental metrics related to an associated entity of the plurality of entities.

14. The method of claim 1, wherein the plurality of APs forms a mesh network.

15. The method of claim 1, wherein a first incident of the incident database corresponds to a vehicle accident, the method further comprising identifying a first device of the plurality of devices with physical and temporal overlap with the vehicle accident based on the correlating.

16. The method of claim 1, wherein a first incident of the incident database corresponds to a crime, the method further comprising identifying a first device of the plurality of devices with physical and temporal overlap with the crime based on the correlating.

17. The method of claim 1, further comprising awarding points in a game based on the correlating.

18. A system comprising:
    a plurality of access points (APs) of a network, the plurality of APs configured to receive beacons from a plurality of devices, each of the plurality of devices having a unique identifier;
    wherein the system is configured to:
       store a plurality of temporal locations associating each of the plurality of devices with associated beacon reception times and beacon reception APs,
       correlate the plurality of temporal locations with an incident database to determine temporal and physical overlap between incidents of the incident database and the plurality of temporal locations; and
       report data based on the correlating.

19. The system of claim 18, wherein the system is further configured to add a first encounter to the incident database when a temporal location of a first device of the plurality of devices is within a predefined proximity of a second device of the plurality of devices and within a physical region associated with an incident of the incident database.

20. The system of claim 18, wherein reporting data based on the correlating comprises providing a first notification to a first device of the plurality of devices having temporal and physical overlap with an incident of the incident database.

21. The system of claim 18, wherein the system is further configured to make incidence data of the incident database accessible to each of the plurality of devices.

22. The system in of claim 18, wherein the system is further configured to add a first encounter to the incident database based on a determination that one or more temporal locations associated with a device of the plurality of devices indicate an elevated risk of exposure to a first incident.

23. The system of claim 22, wherein the first incident comprises transmission of a respiratory virus.

24. The system of claim 18, wherein the system is further configured to:
    associate each of the plurality of devices with a respective entity of a plurality of entities; and
    periodically receive one or more health metrics related to an associated entity of the plurality of entities.

25. The system of claim 18, wherein the system is further configured to:
    associate each of the plurality of devices with a respective entity of a plurality of entities; and
    periodically receive one or more environmental metrics related to an associated entity of the plurality of entities.

26. The system of claim 18, wherein the system is further configured to receive, from a first device of the plurality of devices, first data identifying an entity that has been in close proximity to the first device.

27. The system of claim 26, wherein the first data is further indicative of the length of time of such proximity.

* * * * *